United States Patent
Ledden

(10) Patent No.: US 10,690,528 B2
(45) Date of Patent: Jun. 23, 2020

(54) MEASUREMENT OF ELECTRIC SIGNALS TO DETECT PRESENCE OR FLOW OF ELECTROACTIVE SPECIES IN SOLUTION

(71) Applicant: SFC Fluidics, Inc., Fayetteville, AR (US)

(72) Inventor: Bradley Thomas Ledden, Fayetteville, AR (US)

(73) Assignee: SFC FLUIDICS, INC., Fayetteville, AR (US)

( * ) Notice: Subject to any disclaimer, the term of this patent is extended or adjusted under 35 U.S.C. 154(b) by 241 days.

(21) Appl. No.: 15/765,867

(22) PCT Filed: Oct. 12, 2016

(86) PCT No.: PCT/US2016/056530
§ 371 (c)(1),
(2) Date: Apr. 4, 2018

(87) PCT Pub. No.: WO2017/066241
PCT Pub. Date: Apr. 20, 2017

(65) Prior Publication Data
US 2018/0283916 A1    Oct. 4, 2018

Related U.S. Application Data

(60) Provisional application No. 62/241,203, filed on Oct. 14, 2015.

(51) Int. Cl.
*G01F 1/64* (2006.01)
*A61B 5/1468* (2006.01)
*G01N 27/403* (2006.01)

(52) U.S. Cl.
CPC .............. *G01F 1/64* (2013.01); *A61B 5/1468* (2013.01); *G01N 27/403* (2013.01)

(58) Field of Classification Search
CPC ....... G01N 15/1218; G01N 2015/1254; G01N 15/1484; G01N 33/48707
See application file for complete search history.

(56) References Cited

U.S. PATENT DOCUMENTS

| | | | |
|---|---|---|---|
| 4,104,913 A | 8/1978 | Cockshott et al. | |
| 4,807,480 A | 2/1989 | O'Neill et al. | |

(Continued)

FOREIGN PATENT DOCUMENTS

JP    60001548 A  *  1/1985  ......... G01N 27/3335

OTHER PUBLICATIONS

Achmann et al., "Miniaturized low temperature co-fired ceramics (LTCC) biosensor for amperometric gas sensing", Sensors and Actuators, No. 135, Aug. 3, 2008 (Year: 2008).*

(Continued)

*Primary Examiner* — David A. Rogers

(57) ABSTRACT

An electrochemical sensor may measure the flow of ions and/or electrochemical species in a solution passing the sensor because the electroactive species will continually come into contact with the electrode and an electric signal will be generated by the combination of diffusion and convection bringing the electroactive species to the electrode. The electric signal measured will vary by concentration of ions and/or electrochemical specie(s) and by flow rate. Flow rate may be measured if the concentration of ions and/or electrochemical specie(s) is known; conversely, the concentration of ions and/or electrochemical species may be measured if the flow rate is known. The sensor may also be used to confirm the delivery of a fluid containing ions and/or electroactive specie(s).

19 Claims, 7 Drawing Sheets

(56) References Cited

U.S. PATENT DOCUMENTS

| | | | | |
|---|---|---|---|---|
| 4,933,048 | A | * | 6/1990 | Lauks .................. G01N 27/301 204/400 |
| 5,174,885 | A | * | 12/1992 | Hayakawa ........... G01N 27/417 204/424 |
| 5,338,429 | A | * | 8/1994 | Jolson ................ G01N 27/4045 204/412 |
| 7,417,418 | B1 | * | 8/2008 | Ayliffe ............... G01N 15/1218 204/603 |
| 7,579,823 | B1 | * | 8/2009 | Ayliffe ............... G01N 15/1218 324/71.1 |
| 7,867,782 | B2 | * | 1/2011 | Barth ............... G01N 33/54353 427/2.11 |
| 8,794,054 | B2 | * | 8/2014 | Gridelet ............. G01N 33/5438 73/24.06 |
| 9,880,123 | B2 | * | 1/2018 | Wilkins ........... G01N 33/54366 |
| 10,429,381 | B2 | * | 10/2019 | Hoffman ............ G01N 33/5438 |
| 2013/0026051 | A1 | * | 1/2013 | Nelson ................ G01N 27/308 205/792 |
| 2013/0261021 | A1 | * | 10/2013 | Bocchi ................. B01L 3/5088 506/9 |
| 2014/0012114 | A1 | | 1/2014 | Zevenbergen et al. |
| 2014/0158540 | A1 | * | 6/2014 | Ohura ............... G01N 33/48721 204/543 |
| 2014/0318966 | A1 | * | 10/2014 | Astier ................ G01N 27/4473 204/452 |
| 2018/0045667 | A1 | * | 2/2018 | Huang ................. G01N 27/327 |
| 2018/0128767 | A1 | * | 5/2018 | Feldman ............ G01N 27/3274 |

OTHER PUBLICATIONS

Blaedel, W.J. et al., "The Tubular Platinum Electrode," Analytical Chem., vol. 35, No. 13, pp. 2100-2103 (Dec. 1963).

Berners, Manfred O.M. et al., "On-Line Measurement of Brain Glutamate with an Enzyme/Polymer-Coated Tubular Electrode," Analytical Chem., vol. 66, No. 13, pp. 2017-2021 (Jul. 1, 1994).

Flanagan, James B. et al., "Digital Simulation of Tubular Electrode Response in Stationary and Flowing Solution," The J. of Phys. Chem., vol. 78, No. 7, pp. 718-723 (1974).

Blaedel, W.J. et al., "Study of the Steady-State Current at Tubular Electrodes in the Micromolar Concentration Region," Analytical Chem., vol. 49, No. 11, pp. 1563-1566 (Sep. 1977).

Bai, Jingwei et al., Fabrication of Sub-20 nm Nanopore Arrays in Membranes with Embedded Metal Electrodes at Wafer Scales, Nanoscale, 6, 8900-8906 (2014).

Luan, Binquan et al., "Base-by-Base Ratcheting of Single Stranded DNA through a Solid-State Nanopore," Phys. Rev. Lett. 104, 238103 (2010).

Blaedel, W.J. et al., "Submicromolar Concentration Measurements with Tubular Electrodes," Analytical Chem., vol. 43, No. 12, pp. 1538-1540 (Oct. 1971).

Extended European Search Report for Application No. 16856064.7 (PCT/US2016/056530), dated Apr. 23, 2019.

Kim, Tae-Hyeong et al., "Flow-Enhanced Electrochemical Immunosensors on Centrifugal Microfluidic Platforms," Lab Chip, 2013, 13, 3747.

Kjeang, Erik et al., "Integrated Electrochemical Velocimetry for Microfluidic Devices," Microfluid Nanofluid (2007) 3:403-416.

\* cited by examiner

MEASUREMENT OF ELECTRIC SIGNALS TO DETECT PRESENCE OR FLOW OF ELECTROACTIVE SPECIES IN SOLUTION

STATEMENT REGARDING FEDERALLY SPONSORED RESEARCH OR DEVELOPMENT

This invention was made with government support under Contract No. W81XWH-09-1-0523 awarded by the United States Department of Defense. The government has certain rights in the invention.

TECHNICAL FIELD

This invention pertains to the use of electrochemical species in a flowing solution to either measure the flow rate of the solution or the concentration of electrochemical species in solution.

BACKGROUND ART

References mentioned in this background section are not admitted to be prior art with respect to the present invention.

The first example is U.S. Pat. No. 6,695,958. This design somewhat resembles the present invention, but is based on a cylinder-shaped cavity with a bottom. Solution is either flowed over or deposited on top of the cavity for detection. The bottom plate does not permit the flow of detectable species through the cylinder-shaped cavity. A key aspect of the present invention is the ease of flow of solution past the electrodes embedded in the walls of the lumen.

The next example is U.S. Pat. No. 7,067,351. This patent describes "A method of forming nanolaminate structures having alternating conductor layers and insulator layers". The scale and fabrication of this method are quite different than the present invention. In addition, this filing does not specify the use of flow past the electrodes for electrochemical sensing, a key aspect of the present invention.

The final example is U.S. Pat. No. 7,703,336. This invention is an electrochemical flow sensor, wherein a first set of electrodes is used to alter the chemistry of the solution to create a detectable species that is detected further downstream by a second set of electrodes. The time of flight of the created species is used to determine flow rate. The present invention uses a single set of electrodes to measure the change in electrochemical signal that result from flow of an inherent electrochemical species. The present invention requires no change in the chemistry of the solution.

DISCLOSURE OF INVENTION

The present invention is an electrochemical sensor. This sensor operates by measuring the change in electrochemical signal generated when solutions with an electroactive species are flowing at different rates. If the concentration of electroactive species is known, this sensor can measure flow. If the flow rate is known, this sensor can be used to measure concentration of electroactive species.

When used to measure flow rate, the sensor presents an advancement over the occlusion sensors currently used in drug delivery pumps, because the sensors will be able to immediately detect altered or no-flow conditions that result from occlusions, leaks, depleted drug supply, and any mechanical or electrical failure resulting in no or reduced flow. In certain implementations this sensor is inexpensive, robust and small, and may detect volumes in the nanoliter to microliter range.

These and other features, objects and advantages of the present invention will become better understood from a consideration of the following detailed description of the preferred embodiments and appended claims in conjunction with the drawings as described following:

BEST MODE FOR CARRYING OUT THE INVENTION

Figure 1A:
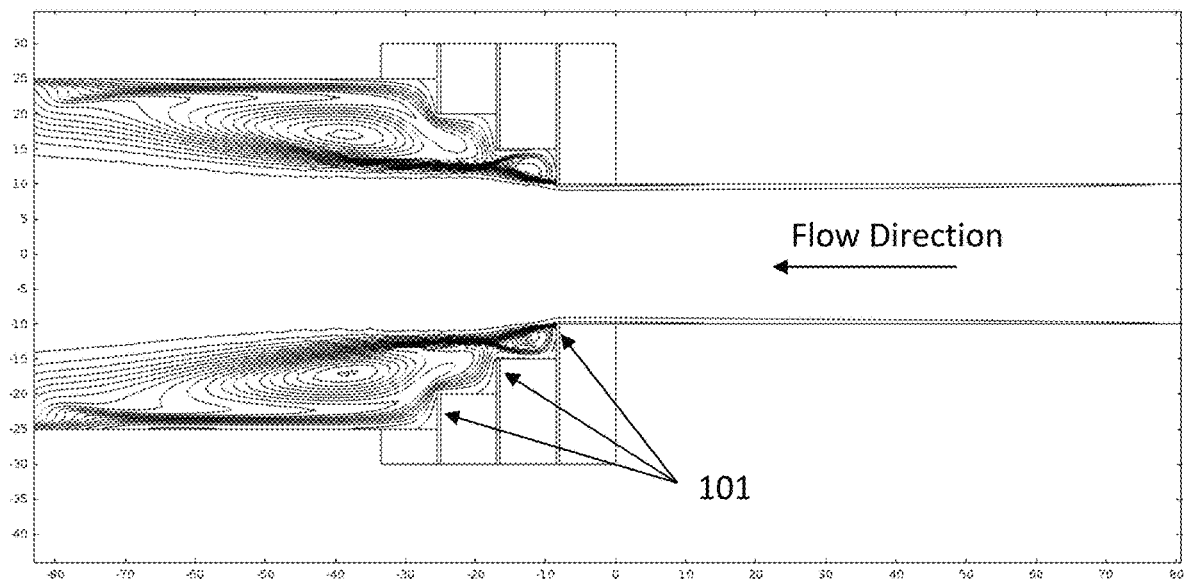
FIG. 1A is a graph depicting the results of a computer simulation of plug flow characteristics flowing through a stepped-wall electrochemical sensor according to an implementation of the invention.

Before the present invention is described in further detail, it should be understood that the invention is not limited to the particular embodiments and implementations described, and that the terms used in describing the particular embodiments and implementations are for the purpose of describing those particular embodiments and implementations only, and are not intended to be limiting, since the scope of the present invention will be limited only by the claims.

When electroactive species are present in solution, electrodes can be used to measure the flow of electrons to or from the electrode from or to ions in the solution. In stagnant solutions, a diffusion-limited depletion layer will eventually develop in the volume of solution immediately adjacent to the electrode and the electric signal will be limited by the rate of diffusion of species to the electrode. However, if the solution is flowing, ions will continually come into contact with the electrode and an electric signal will be generated by the combination of diffusion and convection bringing ions to the electrode. The electric signal measured will vary by concentration of electroactive specie(s) and by flow rate. If one wants to measure flow rate, then concentration of electroactive specie(s) must be known. Conversely, if the concentration of electroactive species is unknown, then the flow rate must be known.

Annular (ring) electrode geometry is one arrangement that permits analytical solutions to the steady state current due to flowing solution; the current measured at such an electrode is given by:

$$i = 2.01 nF\pi C_b D^{\frac{2}{3}} R^{\frac{2}{3}} X^{\frac{2}{3}} V_0^{\frac{1}{3}}$$ Eq 1 where n is the number of electrons per molecule of the electroactive species, F is the Faraday constant, $C_b$ is the concentration of the bulk solution, D is the diffusion coefficient for the electroactive species, R is the internal radius of the electrode, X is the length of the electrode and $V_0$ is the axial flow rate of the solution. This current is derived by solving the 2-D steady-state diffusion equation. To arrive at the above equation several assumptions were made, such as: a linear approximation of the Poiseuille velocity profile, a linear diffusion process in the radial direction, and axial diffusion is neglected. More simply, the current is composed of two parts: a current at zero flow rate (diffusion limited); and a current dependent on convection. The total current takes the form:

$$i_T = i_{ind} + k v_f^{1/3}$$ Eq 2 where $i_{ind}$ is the current independent of flow rate (zero flow), and $$k v_f^{1/3}$$

is a restatement of the flow rate dependent current from Eq 1 where all non flow rate variables are represented by the constant k.

Great progress has recently been made in the fabrication of microstructures. For the annular ring geometry, the inventor has found that a good fabrication method is the use of Low Temperature Co-fired Ceramic (LTCC) methods. LTCC fabrication can be classified as a meso-scale fabrication technique where critical features can be on the order of 100 μm while the entire structure can be several cm² in area without great cost. Especially, it has been found that for an annular ring geometry, it is unlikely a similar structure could be built by current thin-film microfabrication methods.

Screen-printed electrodes with a 3-D fabrication of electrochemical sensors in LTCC have been reported. Those electrodes were made along the sides of a long rectangular channel and are likely to trap bubbles. LTCC and screen printed gold electrodes on the sides of rectangular channels have also been demonstrated for magnetohydrodynamic studies. While planar screen printed electrodes have been demonstrated and are commercially available, no known design incorporates annular electrodes, where the electrodes are built into the walls of a channel and solution flows through the channel and ring electrodes. This design prevents bubble trapping and promotes fluid flow. The advent of high purity noble metal inks and lamination type fabrication methods permits the facile design and fabrication of ring electrodes for microfluidic applications. It should be noted that the convenience of the use of ring electrodes in a tubular lumen does not preclude the use of similar structures in lumens of any shape, including oval, square or other flow path shapes.

Fabrication of ring electrodes embedded in the walls of a channel reduces the problem of trapped bubbles and permits the use of inexpensive disposable noble metal electrodes. LTCC fabrication according to an implementation of the invention is carried out by screen printing conductive inks onto a silica and alumina "green" sheet. Several of these sheets are then laminated together under high pressure. The assembled product is then pyrolyzed at a temperature of 200-500° C., during which the organic binding agents used in the ink and green tape are burned off. After this baking step, the LTCC assembly is heated to a peak temperature of 850-900° C., during which the metal ink is fused into a conducting electrode and the silica is sintered leaving behind a hard, coherent structure.

Figure 1B:
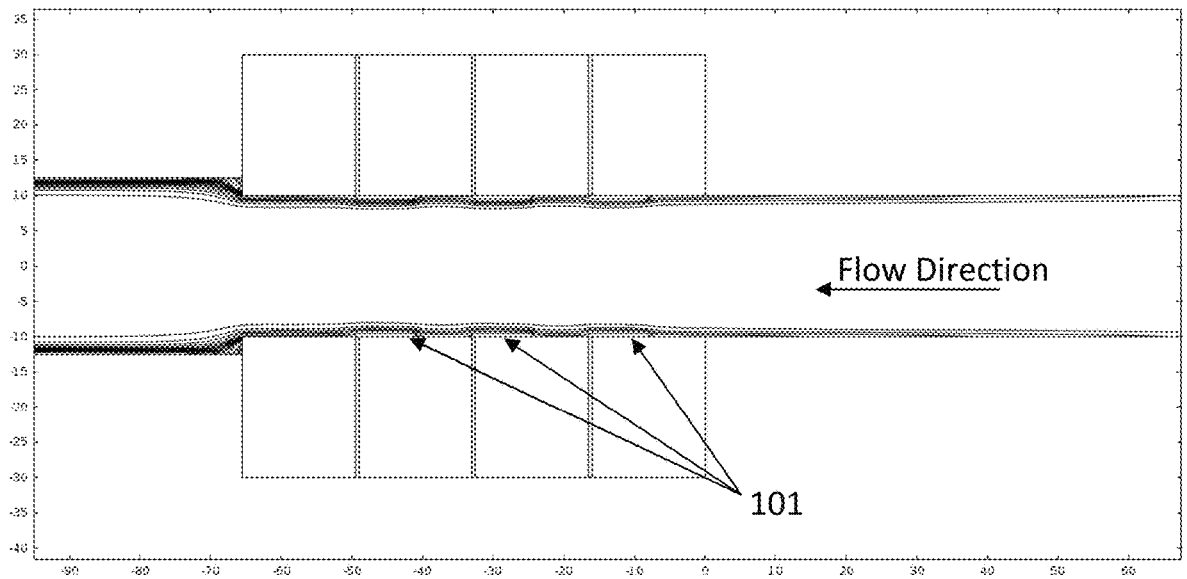
FIG. 1B is a graph depicting the results of a computer simulation of plug flow characteristics flowing through a smooth-walled electrochemical sensor according to an implementation of the invention.

While nearly any electrode diameter could have been chosen in various implementations, in one implementation of the invention a diameter of 500 μm (20 mil) was chosen. This diameter is identical to the diameter of tubing used in many miniature drug delivery devices. To determine which geometry was best suited for measurement of the electric signal, two annular geometries were examined by simulation. To reduce computation time, two-dimensional simulations were performed. Cross sections of these are shown in FIG. 1. The first geometry (FIG. 1A) is a stepped design. The benefit of this design is the relaxed alignment of the central lumen and a relatively larger electrode area (101) compared to design 2 (FIG. 1B). Design 1 was deemed most likely to be fabricated reliably. Design 2 had more stringent requirements on alignment but presented the lowest opportunity for bubble trapping. These two different annular geometries were examined with COMSOL computer modeling. FIGS. 1A and 1B show the structure of the simulated electrodes with equiconcentration lines showing the different distances between high and low concentration areas. Both designs were given the same initial concentration of species of 0 M solution simulating plain water. Flow was pressure driven with an inlet pressure of 30 Pa. The concentration of incoming species was 1 M and the time required for electrodes to be fully bathed in 1 M solution was monitored.

The stepped wall design shown in FIG. 1A has three electrodes (101) with three different electrode areas. The dimensions of the electrodes were chosen based on dimensions that could readily be achieved and aligned. Electrode area of the first electrode is simply the area of a disk with radius of 15 mil (381 μm) minus the area of a 10 mil (254 μm) radius disk.

$$A_i = \pi(381 \ \mu m)^2 - \pi(254 \ \mu m)^2 = 0.253 \ mm^2$$ Eq 3

$$A_{ii} = \pi(508 \ \mu m)^2 - \pi(381 \ \mu m)^2 = 0.355 \ mm^2$$ Eq 4

$$A_{iii} = \pi(635 \ \mu m)^2 - \pi(508 \ \mu m)^2 = 0.4563 \ mm^2$$ Eq 5

This step design places constraints on the assignment of electrodes in such a device. The counter electrode area should be equal to or larger than the working electrode area. In addition, the reference electrode should be placed upstream of the working and counter electrodes, in a three-electrode cell. The reference electrode is the electrode that the applied potential of the working electrode is measured with respect to, thus it is important no electrochemistry has been performed to alter potential on the reference electrode. The counter electrode has a potential opposite the working electrode and serves to complete the electrical circuit. Since current is not measured through the counter electrode, convention is to increase the size of the counter with respect to the working electrode so the reaction is only limited by what occurs on the working electrode. This forces the solution to flow into the narrow end of the sensor first. Finally, this design increases the volume necessary to fill the structure. The calculated volume in design 1 was 0.547 µl. The concentration of species after a simulated time of 0.6 seconds of this flow is shown in FIG. 1A, with equiconcentration lines from 1M in the center of the channel on the right hand side. It is evident that after a simulated time of 0.6 seconds, the incoming species do not fully cover the reference electrode (rightmost), much less the working (center), and counter (leftmost). The formation of stagnation zones near the surface of the electrodes (101) slows the response of the sensor to the initiation of flow.

The other geometry studied is shown in FIG. 1B. The smooth-walled design has three electrodes with identical sizes given by:

$$A_{band}=(2\pi\ r\ h)=(2\pi*0.254\ mm)*0.2\ mm=0.319\ mm^2 \qquad \text{Eq 6}$$

Having all three electrodes with the same area is less than ideal, but the inventor has found that such a sensor design can be made to work. The smooth-walled design does allow the modification of adding an additional layer to increase the counter electrode area by a factor of two. Indeed, the area of all electrodes can be changed by including additional layers. As modeled, this geometry had a volume of 0.162 µl or about 30% of the volume of Design 1. Again, the initial concentration of species was 0 M, with pressure driven flow of 30 Pa, and incoming species at concentration of 1 M. FIG. 1B shows the concentration profile after 0.6 seconds, the same time as FIG. 1A for the stepped-wall design. It is evident that the concentration profile is better developed with high concentration solution touching all three of the electrodes. (101)

Based on these computer simulations, the stepped-side wall design was not pursued further due to the persistent occurrence of low concentration depletion zones around the electrodes (101) and the increased volume to fill the detector. The equiconcentration lines in the figure indicate that there are large portions of the electrode surfaces that are far from an area of high analyte concentration. An electrochemical sensor with this configuration would be less sensitive to small volume plugs of analyte. The smooth side wall design, on the other hand, does not have the large stagnation zones near the electrodes. In fact the electrodes protrude, by the thickness of the ink layer, into the analyte flow stream.

The boundary layer in this design presents a much lower impediment to the sensing of the correct concentration than the depletion zones present in the stepped design. The desire to develop a sensor that responded quickly to the lowest volume of analyte favored the smooth-walled design despite the increased difficulty of alignment. Specific applications, however, may favor the stepped-wall design. Other geometries have not yet been pursued, but could be developed as alternative implementations of the invention. One possible alternative is the use of differing number of electrodes. A two electrode configuration, where reference and counter electrodes are combined, may be possible but was not explored here. The difficulty in a two electrode arrangement is that for best stability the pseudo reference electrode needs to be exposed to solution that has not undergone electrochemical changes. Additionally, interdigitated electrode designs could be possible with the addition of more electrode and insulating layers. Finally, multiple electrodes would allow for redundancy or modify the sensitivity by altering the size of the electrodes.

Figure 2:
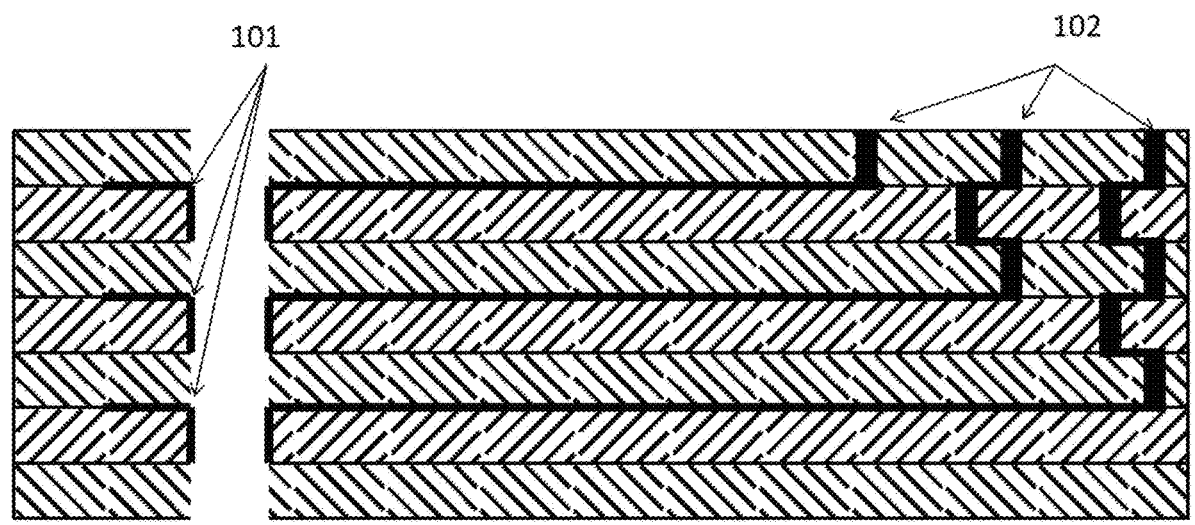
FIG. 2 is a side view of an electrode assembly according to an implementation of the invention.
Figure 3A:
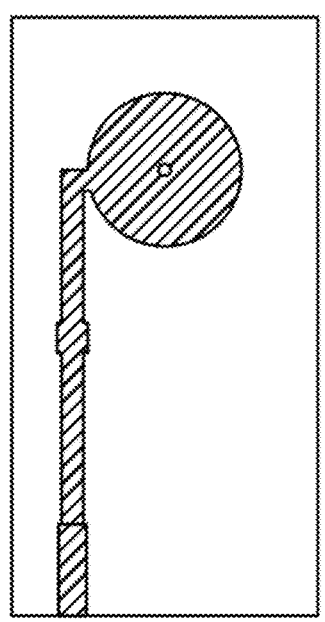
FIGS. 3A, 3B, and 3C depict mask designs for ring electrodes on Low Temperature Co-fired Ceramic (LTCC) green sheet layers according to an implementation of the invention.
Figure 3B:
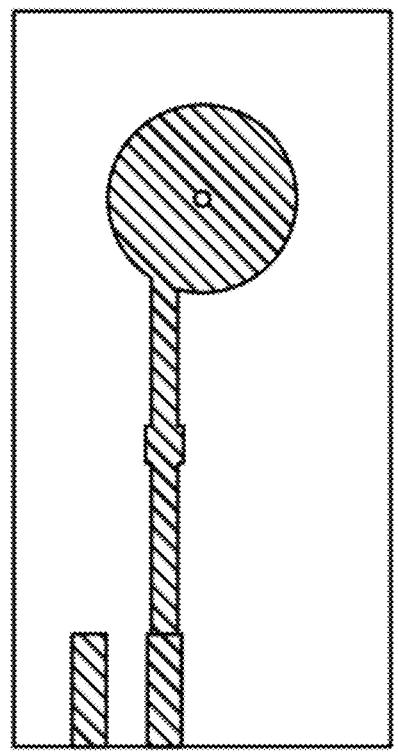
Figure 3C:
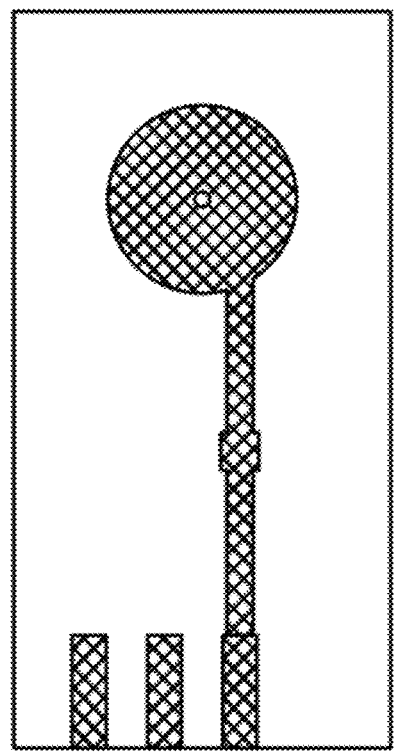

According to an implementation of the invention, sensors were fabricated using LTCC methods. LTCC fabrication is essentially a lamination process. Each green sheet (DuPont 951PX) was punched with a 575 µm diameter via that served as the lumen through which fluid will later pass. In addition, 12 mil diameter vias were also punched above the contact leads to allow electrical connection from lower levels up to the top of the structure. A side view of the structure is shown in FIG. 2. A top-down view of the three electrodes is shown in FIGS. 3A, 3B, and 3C. The LTCC green tape is screen printed with the patterns shown in FIGS. 3A, 3B, and 3C. The connection vias pass through the interim layers as depicted in FIG. 2 and up to the top layer. Each electrode layer presents a connection pad for the layers beneath it. Briefly, the layers of green tape were screen printed with designs show in FIG. 3. The bottom electrode in the lamination was screen printed in the pattern of FIG. 3A. The hatched areas define where the ink was printed, with the hole in the hatched disk defining the location of the punched-through via. Atop this layer an LTCC sheet was placed with the main fluid via as well as small electrical connection vias punched. The second electrode in the lamination was printed with the design in FIG. 3B. Again the hole in the large circle denotes the position of the fluid passage. In FIG. 3B there are two pads for electrical connection to the electrode structure. The right connection pad connects to the second electrode, while the left connection pad connects to the bottom electrode through the electrical connection vias punched and filled in the interposing insulation layer. The process was continued for the final electrode whose screen print pattern is shown in FIG. 3C.

Figure 4:
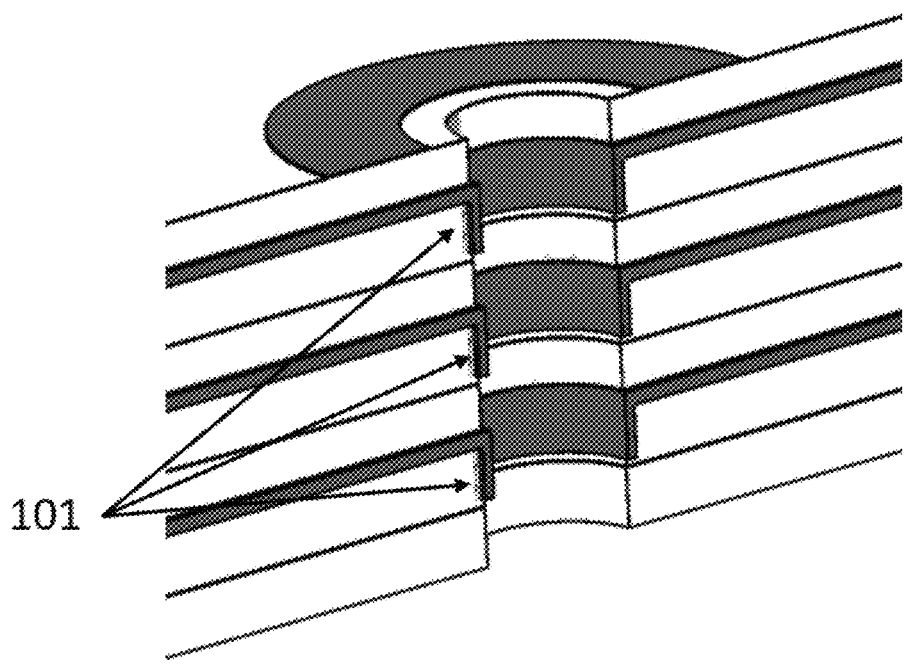
FIG. 4 is a drawing showing a cut-away view of a central lumen in an electrochemical sensor according to an implementation of the invention.

At the outset, it was unknown if the screen printed ink would evenly coat the inside of the lumen, so test structures were fabricated utilizing lower cost silver ink (DuPont 6142D). The layers of green tape were then laminated together with insulating layers in between the electrode layers for a total of seven layers, as shown in FIG. 2. The layers are laminated using isostatic pressure and fired according to protocols published by DuPont. A cross-sectional drawing of a test structure fabricated with silver ink is shown in FIG. 4. It can be seen that the ink flows into the lumen and forms a well-defined annular electrode (101) with the thickness of the LTCC sheet defining the width of the annular electrode. The distance between the electrodes is likewise defined by the thickness of an insulating LTCC sheet that is not screen printed except to fill the electrical connection vias, and to provide "landing pads" for via to via connection. Tests performed with the silver ink confirmed that the design yielding the best results in simulation could be realized in practice. By varying the thickness or number of the LTCC layers it is possible to alter the spacing of the electrodes. Additionally, it is possible to stack the three screen-printed features shown in FIG. 3 to create an interdigitated design, or increase the area of the counter electrode.

Previous testing of commercially available screen printed gold electrodes revealed undesirable peaks when testing low concentration analytes. The inventor suspects that the quality of the gold ink used in these electrodes was poor and the peaks seen in cyclic voltammetry were stripping peaks of unknown contaminants. To eliminate these interferences, DuPont TC502 gold ink was chosen to make the electrodes used for electrochemical testing because of its claimed high purity. Upon firing, the carbon residue in the ink is burned off leaving behind gold electrodes. Testing revealed that the TC502 ink did not produce unwanted peaks when performing electrochemical tests on low-concentration analytes. For the chips tested electrochemically, each electrode (Reference, Working, and Counter) was fabricated by screen printing gold ink on the separate layers. The insulating layers were also printed with gold ink away from the central lumen to fill connection vias. The electrodes were laminated and fired by the same method as the silver test structures. DuPont literature for the 951 LTCC green tapes specifies a shrinkage rate of 12.7% in the x-y plane after lamination and firing. To account for this, the central via was designed and punched with a diameter of 575 μm to yield a diameter of 500 μm in the finished part. After lamination and firing, the central lumen was found to be 445+/−6 μm in diameter which is attributable to 23.5% shrinkage during firing. The increased shrinkage may be attributable to the low amount of ink printed per sheet, or the low number of sheets laminated. This yields an electrode area of approximately 0.03 mm² based on a post firing layer thickness of 200 μm. For simplicity, all three electrodes were fabricated to be the same width, although this need not be the case in alternative implementations of the invention.

While this implementation of the invention was constructed utilizing sensors manufactured using LTCC, it would also be possible to utilize other manufacturing techniques in alternative implementations. One such approach would be to use technology that permits the printing of conductive inks on plastic substrates. Another approach would be the fabrication of multiple layers with thin-film techniques such as evaporated gold and polyimide and then etching through the layers to reveal the ring electrode structure.

Before electrochemical testing of the implementation described above, the chips were cleaned by soaking in KOH $H_2O_2$ solution and performing cyclic voltammetry (CV) sweeps in KOH solution until the CV curves overlapped.

Figure 5A:
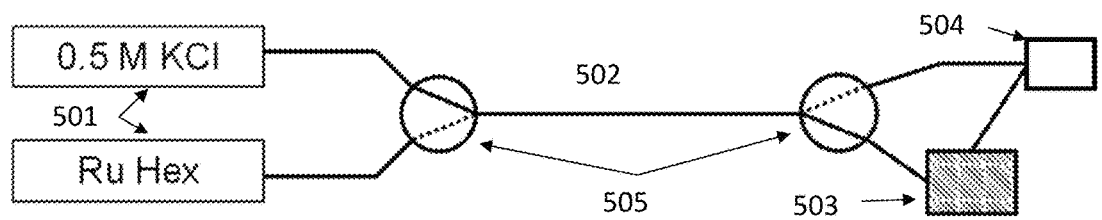
FIG. 5A is a schematic diagram showing a flow sensor configuration according to an implementation of the invention.
Figure 5B:
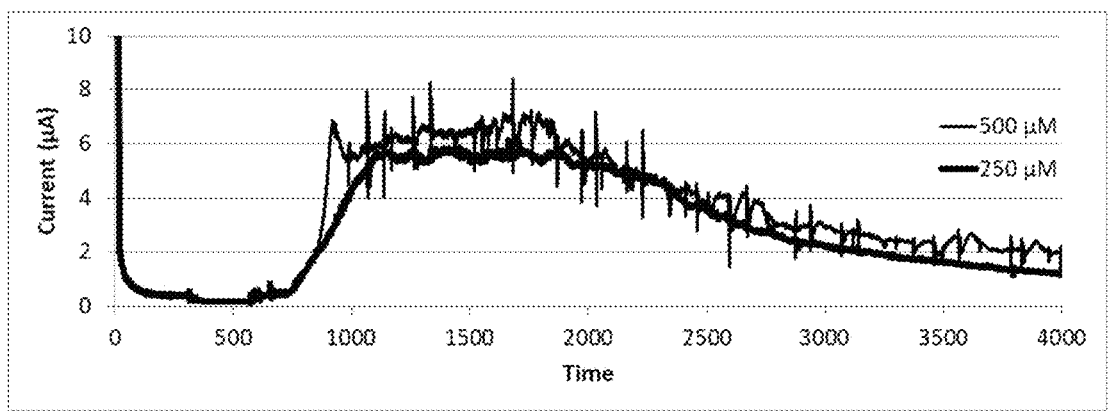
FIG. 5B is a graph depicting data taken with chronoamperometry of two concentrations of ruthenium hexamine using the configuration depicted in FIG. 5A.

The sensor as described herein can operate as a flow-through sensor for detection of upstream generated electrochemical species. In this mode, the flow rate as a function of time is known, but the type and concentration of the electrochemical species may be unknown. An example of this configuration is shown in FIG. 5A. Both 0.5 M KCl and 0.5M KCl, with Ruthenium hexamine are loaded into syringes (501). KCl without RuHex is flowed through the sample loop (502), flow through sensor (503), and into a waste bottle (504). Then, both valves (505) are switched so KCl with ruthenium hexamine is flowed through the sample loop (502) and into the waste bottle (504). For detection as shown in FIG. 5B, both valves (505) are switched back and 0.5 M KCl is pumped through. The sensor (503) is thus exposed to residual 0.5 M KCl after the second valve, then 100 μl of solution containing ruthenium hexamine followed by 0.5 M KCl FIG. 5B shows data of two RuHex plugs passing through the detector at the same flow rate. The thicker curve corresponds to 100 μl of 250 mM RuHex 0.5M KCl. The thinner curve is the signal from 100 μl of 500 mM RuHex 0.5M KCl. In both cases the sensor is filled with 0.5M KCl at the beginning of the test, the plug of RuHex flows through, followed by 0.5M KCl.

Figure 6:
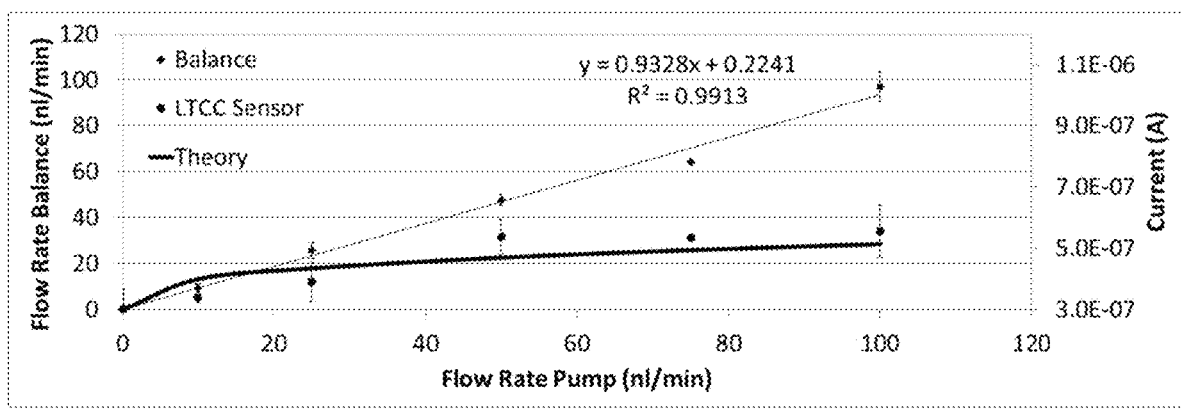
FIG. 6 is a graph of current measured by chronoamperometry at low flow rates using an implementation of the invention.

To better explore the enhanced convection and hence increased current present at very low flow rates, chronoamperometry (CA) studies were used. In this setup, the working electrode is constantly biased and the flow of current is proportional to the rate at which species are brought to the electrode surface by convection. Initially, it was decided to measure the current generated at the electrode surface without the presence of electroactive species. The data from this experiment is shown in FIG. 6. This data was recorded by a CHI 1030 with a bias of −1.0 V applied to the working electrode referenced to the on-chip reference electrode. The on-chip counter electrode was used as well. The flow is generated by an ePump Model 190 (SFC Fluidics), which exhibits no pulses during pumping. Flow rate was verified by a Sartorius SE2 ultramicrobalance (0.0001 mg resolution). Briefly, after solution flowed through the electrode it was flowed into a cup positioned on the balance which has been modified for the measurement of very low flow rates. The draft shield was replaced with a similar shield which has a 360 μm diameter fused silica tube (Idex Health Sciences) fixed into the top, which protrudes down into a small fluid reservoir. The water in the reservoir is covered with high purity mineral oil (PML Microbiologicals) to eliminate measurement error due to evaporation. The tube extends through the oil into the water without touching the walls or bottom of the reservoir. By measuring the change in mass of the solution, the flow rate of the pump was confirmed. FIG. 6 shows the current measured by the electrode as well as the flow rate confirmed by the ultramicrobalance in relation to the intended flow rate plotted on the x-axis. Based on measurements with the ultramicrobalance, the ePump Model 190 is able to produce flow rates as low as 10 nl/min with both high precision and accuracy. Flow rates below this were not tested. In this case, the current measured is proportional to the rate at which charge carriers ($K^+$, $Na^+$, $Cl^-$) are carried to the electrode. The sensitivity for the electrochemical measurements is less than the balance since the current is proportional to $v^{1/3}$ while mass is proportional to v. However, the electrode requires much less space and requires much less sophisticated measurement electronics.

The current measured in the annular electrodes is of the form predicted by Eq 2, where:

$$i_T = i_{ind} + kv^{1/3}$$

According to Eq 1 the constant k should be:

$$k = 2.01 \; nF\pi C_b D^{2/3} R^{2/3} X^{2/3}$$

Where $C_b$=0.140 mol/L, D=1×10⁻⁷ cm²/sec, R=0.025 cm, and X=0.02 cm. For the implementation described herein, this yields:

$$i_T = 3 \times 10^{-9} \; A + 1.8 \times 10^{-5} \; (C \cdot \sec^{-2/3} \cdot cm^{-1}) \cdot v^{1/3} \quad \text{Eq 8}$$

Figure 7A:
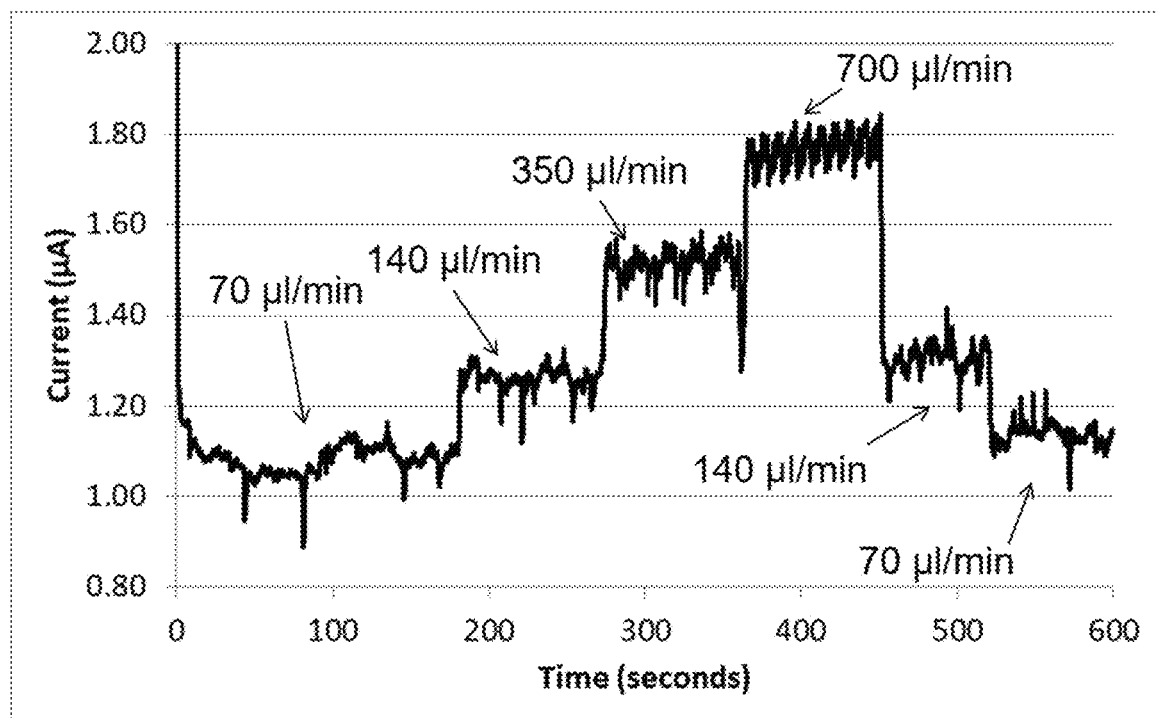
FIG. 7A is a graph showing a variation of current against pumping rate in an implementation of the invention.
Figure 7B:
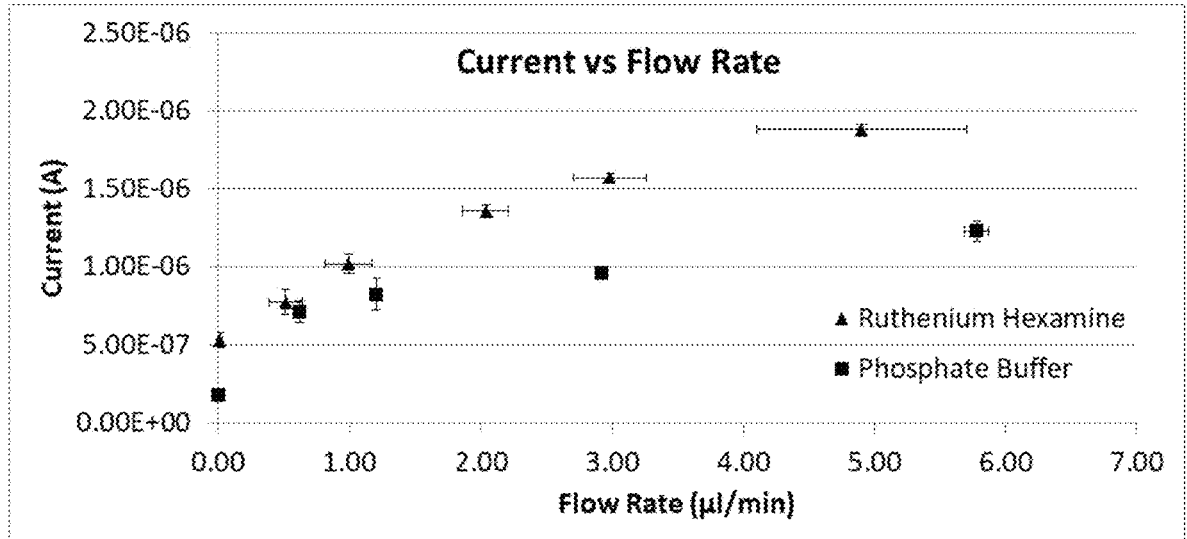
FIG. 7B is a graph showing average current against flow rate for multiple runs with two possible solutions according to an implementation of the invention.

A line with this value is plotted in FIG. 6, while experimentally determined values are plotted as squares, which shows good agreement. Due to the simple design and the closed-form solution predicting current based on flow rate, annular electrodes can serve as flow sensors for microfluidic applications where robustness and simplicity are needed. Because of the proportionally larger change from no flow to flowing conditions, the ring sensor could easily serve as a flow/no-flow occlusion sensor. The incorporation of more sensitive control and sensing electronics also permits using the ring electrode as a sensor to discriminate between different flow rates of a solution with a known concentration of electroactive species. Similar data is shown in FIGS. 7A, 7B, 8A, and 8B. FIG. 7A shows the current passing through the detector at different flow rates similar to the data seen in FIG. 6. FIG. 7B shows average currents passing through the detector at different flow rates. The squares are current vs. flow rate for Phosphate buffer solution, while the triangles are current vs. flow rate for 1 mM RuHex solution, a model electroactive compound.

Figure 8A:
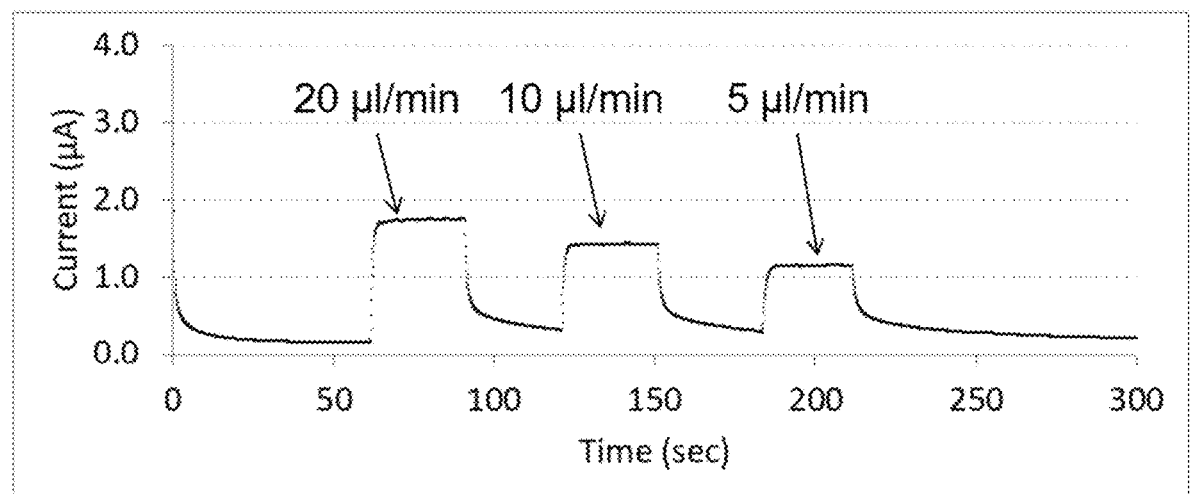
FIG. 8A is a graph showing sensor response to flow of PBS solution with the addition of 0.2% m-cresol with current plotted against time with different flow rates labeled in an implementation of the invention.
Figure 8B:
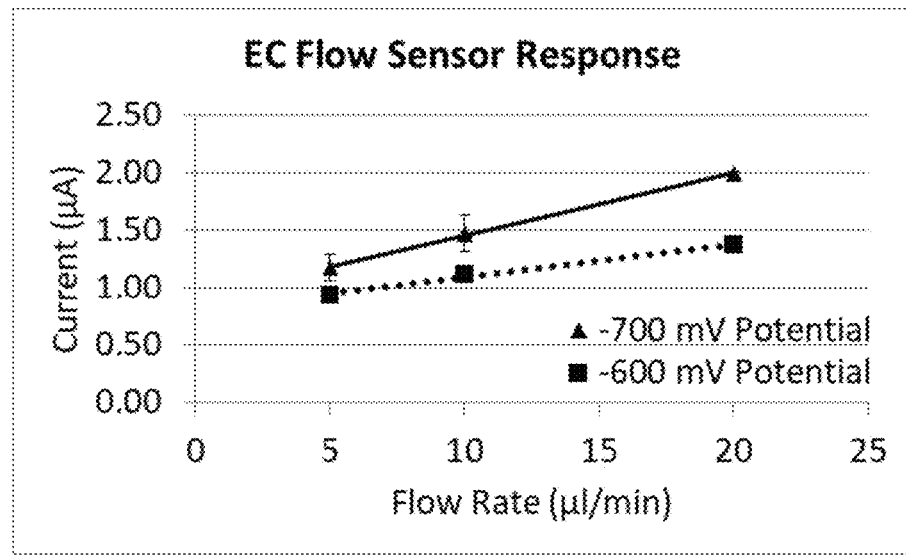
FIG. 8B is a graph showing sensor response to flow of PBS solution containing 0.2% m-cresol with current plotted against flow rate at two different potentials according to an implementation of the invention.

In addition to flow rate determination for model electrochemical species, the annular ring electrode can also be used to determine the flow rate of other electroactive compounds. FIGS. 8A and 8B show data collected from PBS buffer with the addition of 0.2% m-cresol. Similar concentrations of m-cresol act as a preservative in some insulin formulations. The graph of FIG. 8B shows the average current vs. flow rate for two different potentials applied to the working electrode of the flow-through sensor. For this concentration and flow rate regime the current from the annular ring electrodes is roughly linear with flow rate. The electrode can act as an independent flow confirmation sensor. Since the concentration of the electroactive species is known, variations in signal amplitude correspond to solution flow rate. By also measuring the duration of enhanced signal the volume (flow rate*time) of drug delivered can be determined. This signal is independent from the cause of flow, and may be used to confirm dosing by a variety of pumping mechanisms. The ability of the sensor to shed bubbles is advantageous for this measurement. Bubbles trapped on the electrode surface effectively limit the area in contact with the solution causing variation in signal amplitude. Variations in amplitude would in turn lead to variability in calculated delivered dose.

Even though it is a preferred embodiment, it is not required that solution pass through an electrode embedded in a lumen for flow confirmation. An electrode could be placed near where a solution with electroactive species enters a larger volume and still be capable of confirming flow. In this instance, solution would flow through a cannula and electroactive species in the solution would be dispensed near an electrode. The electrode would measure a change in the concentration of electrochemical species indicative of dispense of the solution into the larger volume. Electrochemical species are added to many solutions as preservatives; one such application is the addition of ascorbic acid to food to serve as an oxygen scavenger. Another example is the addition of m-cresol or phenol as a preservative in insulin. Lack of confirmation of dispense of solutions with electroactive species would identify occlusion, or other dispense errors. If the signal measured by the electrode is proportional to dispense volume, then the signal could permit closed-loop confirmation of dispense volume and timing of dispense. For a simpler flow/no-flow indication a two electrode implementation may be sufficient. Such a system may be used to warn of dispense errors such as occlusions, kinks in tubing, leaks, depleted drug supply, or any mechanical or electronic failure. The electrode need not be annular rings, which are most effective at sensing the fluid inside the lumen. Other designs, such as interdigitated, or even simpler planar geometries may be more suited to confirming dispense of solutions with electroactive species. One such possible implementation of the invention is inserting an electrode very near to the cannula used for drug delivery to a patient. When the electrode is connected to control electronics, dispenses of drug containing electrochemical species will result in an altered signal from the electrode. This signal confirms that drug has been delivered to the patient. This permits the electronics controlling the dispense mechanism to report independent confirmation of drug delivery.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. When a grouping is used herein, all individual members of the group and all combinations and subcombinations possible of the group are intended to be individually included. When a range is stated herein, the range is intended to include all subranges and individual points within the range. All references cited herein are hereby incorporated by reference to the extent that there is no inconsistency with the disclosure of this specification.

The present invention has been described with reference to certain preferred and alternative embodiments that are intended to be exemplary only and not limiting to the full scope of the present invention, as set forth in the appended claims.

The invention claimed is:

1. An electrochemical sensor, comprising:
   a. a first ring electrode comprising a first electrode annular section;
   b. a second ring electrode adjacent to the first electrode and comprising a second electrode annular section,
   c. a first insulator between the first electrode and the second electrode;
   d. a third ring electrode adjacent to the second electrode and comprising a third electrode annular section;
   e. a second insulator between the second electrode and the third electrode; and
   f. a lumen in which the electrodes are embedded, wherein the sections of the electrodes comprise an opening that is the same shape as the lumen in which they are embedded, and wherein the first, second, and third electrode annular sections and insulators are aligned such as to provide a flow path for a fluid through the lumen, the fluid comprising one or more of ions or electrochemical species whereby the electrodes are configured to measure an electrical signal from the fluid.

2. The electrochemical sensor of claim 1, further comprising at least one additional ring electrode separated by an insulating layer from any other ring electrode.

3. The electrochemical sensor of claim 1 wherein each of the electrodes comprise:
   a. at least one green sheet comprising at least one of glass or ceramic; and
   b. conductive inks on the surface of the at least one green sheet.

4. The electrochemical sensor of claim 1, wherein the electrochemical sensor comprises a plurality of insulating sheets laminated together with conductive inks printed on at least some of the plurality of insulating sheets.

5. An electrochemical sensor, comprising:
   a. a lumen;
   b. a first ring electrode comprising a first electrode annular section, wherein the first ring electrode is embedded in the lumen;

c. a second ring electrode adjacent to the first electrode and comprising a second electrode annular section, wherein the second ring electrode is embedded in the lumen;

d. a first insulator between the first electrode and the second electrode, wherein the first insulator is embedded in the lumen;

wherein the first and second electrode annular sections and first insulator are aligned such as to provide a flow path through the lumen for a fluid comprising one or more of ions or electrochemical species therethrough whereby the electrodes are configured to measure an electrical signal from the fluid, and wherein the sections of the electrodes and insulator comprise an opening that is the same shape as the lumen in which they are embedded.

6. The electrochemical sensor of claim 5, further comprising at least one additional ring electrode separated by an insulating layer from any other ring electrode.

7. The electrochemical sensor of claim 5 wherein each of the electrodes comprise:
   a. at least one green sheet comprising at least one of glass or ceramic; and
   b. conductive inks on the surface of the at least one green sheet.

8. The electrochemical sensor of claim 5, wherein the electrochemical sensor comprises a plurality of insulating sheets laminated together with conductive inks printed on at least some of the plurality of insulating sheets.

9. A method of measuring a concentration of one or more ions or electrochemical species in a fluid, comprising the steps of:
   a. measuring a flow rate of the fluid through a lumen;
   b. passing the fluid through a plurality of ring electrodes positioned such that the lumen passes through the ring electrodes;
   c. applying an electric stimulus to at least one ring electrode;
   d. measuring the resultant electrical signal from at least one of the ring electrodes; and
   e. determining the concentration of the one or more ions or electrochemical species in the fluid based on the flow rate and the measured electrical signal.

10. A method of measuring a flow rate of one or more ions or electrochemical species in a fluid with a known concentration of ions or electrochemical species, comprising the steps of:
    a. passing the fluid through a lumen;
    b. passing said fluid through a plurality of ring electrodes positioned such that the lumen passes through the ring electrodes;
    c. applying an electrical stimulus to at least one ring electrode;
    d. measuring the resultant electrical signal from at least one of the ring electrodes; and
    e. determining the flow rate of the fluid based on the concentration of the ions or electrochemical species in the fluid and the measured electrical signal.

11. The method of claim 10, further comprising the step of determining that a reduced or no-flow rate indicates occlusion, fluid depletion, pump failure, valve failure or other system failure.

12. The method of claim 10, wherein the fluid comprises a drug, hormone, or medication for delivery to a patient.

13. The method of claim 12, wherein the fluid comprises at least one of insulin or glucagon.

14. The method of claim 12, wherein the fluid is comprised of one or more ions or electrochemical species.

15. A method of detecting the presence of one or more ions or electrochemical species in a fluid, comprising the steps of:
    a. passing a fluid through a lumen, wherein the lumen terminates very near to a plurality of electrodes;
    b. applying an electric stimulus to at least one electrode;
    c. measuring the resultant electrical signal from at least one of the electrodes; and
    d. determining from the electrical signal whether the fluid containing ions or electrochemical species has been delivered to the electrodes.

16. The method of claim 15, further comprising the step of determining that a no delivery or reduced delivery of fluid indicates occlusion, fluid depletion, pump failure, valve failure, or other system failure.

17. The method of claim 15, wherein the fluid comprises a drug, hormone, or medication for delivery to a patient.

18. The method of claim 17, wherein the fluid comprises at least one of insulin or glucagon.

19. The method of claim 17, wherein the fluid is comprised of one or more ions or electrochemical species.

* * * * *